United States Patent
Brown et al.

(10) Patent No.: US 6,201,039 B1
(45) Date of Patent: *Mar. 13, 2001

(54) BONE SUBSTITUTE COMPOSITION COMPRISING HYDROXYAPATITE AND A METHOD OF PRODUCTION THEREFOR

(75) Inventors: Paul W. Brown, State College, PA (US); Kevor S. Ten Huisen, Neshanic Station, NJ (US); Roger I. Martin, Denver, PA (US)

(73) Assignee: The Penn State Research Foundation, University Park, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 00 days.

(21) Appl. No.: 08/617,809

(22) PCT Filed: Sep. 20, 1994

(86) PCT No.: PCT/US94/10604
§ 371 Date: Jun. 24, 1996
§ 102(e) Date: Jun. 24, 1996

(87) PCT Pub. No.: WO95/08304
PCT Pub. Date: Mar. 30, 1995

Related U.S. Application Data (63) Continuation-in-part of application No. 08/124,731, filed on Sep. 21, 1993, now abandoned.

(51) Int. Cl.[7] .................................................. A61F 2/28
(52) U.S. Cl. ................................ 523/115; 424/423
(58) Field of Search .......................... 424/423; 523/115, 523/116

(56) References Cited

U.S. PATENT DOCUMENTS

| 3,767,437 | * 10/1973 | Cruz, Jr. . |
| 3,929,971 | * 12/1975 | Roy . |
| 4,548,959 | * 10/1985 | Nagai et al. . |
| 4,795,467 | * 1/1989 | Piez et al. . |
| 5,496,399 | 3/1996 | Ison et al. . |

FOREIGN PATENT DOCUMENTS

| 1-111762 | 4/1989 | (JP) . |

OTHER PUBLICATIONS

Thesis, The Formation of Biocomposites at Physiological Temperatures, Kevor S. Ten Huisen, The Pennsylvania State University, Shelved Nov. 18, 1992.

TenHuisen et al., Journal of Biomedical Materials Research, vol. 28, 27–33 (1994).

* cited by examiner

*Primary Examiner*—Carlos Azpuru
(74) *Attorney, Agent, or Firm*—Thomas J. Monahan

(57) ABSTRACT

The present invention is directed to polymineralic particles which are precursors of hydroxyapatite and a method for their production. The present invention is also directed to a synthetic bone-like composition comprising said hydroxyapatite polymineralic precursor particles of hydroxyapatite and optionally, a polymeric material capable of promoting mineralization of hydroxyapatite, which are useful for fixing prosthetic devices, useful as bone substitutes to directly fill bone defects, to provide substrates for cartilage, and to repair teeth, and methods of making such preparations. The present invention is also directed to a method of treating collagen to provide a micro-structure close to that of native bone.

22 Claims, 5 Drawing Sheets

THE TERNARY PHASE SYSTEM: $P_2O_5$–$Ca(OH)_2$–$H_2O$ SHOWING THE STABILITY REGIONS FOR VARIOUS CALCIUM PHOSPHATES.

THE TERNARY PHASE SYSTEM: $P_2O_5-Ca(OH)_2-H_2O$ SHOWING THE STABILITY REGIONS FOR VARIOUS CALCIUM PHOSPHATES.

COMPARISON OF THE RATES OF HAp FORMATION, AS DETERMINED BY THE RATES AT WHICH HEAT IS EVOLVED, DEPENDING ON THE PRESENCE OF COLLAGEN.

FIG. 5A

HEAT EVOLUTION CURVES (a) SHOWING THAT ACETIC ACID SOLUTIONS ACCELERATE HAp FORMATION AND (b) THAT CITRIC ACID SOLUTIONS DECELERATE THE RATE OF HAp FORMATION.

FIG. 5B

BONE SUBSTITUTE COMPOSITION COMPRISING HYDROXYAPATITE AND A METHOD OF PRODUCTION THEREFOR

The present application is a §371 application of PCT/US94/1064 filed Sep. 20, 1994, which is a continuation-in-part of application Ser. No. 08/124,731 filed Sep. 21, 1993, now abandoned.

GOVERNMENT SPONSORSHIP

This invention was made with Government support under rant No. BCS-8908631 awarded by the National Science Foundation. The Government has certain rights in the invention.

BACKGROUND OF THE INVENTION

1. Field of the Invention

The present invention is directed to polymineralic particles which are precursors of hydroxyapatite and a method for their production. The present invention is also directed to a synthetic bone-like or dental composition comprising said hydroxyapatite polymineralic precursor particles of hydroxyapatite and optionally, a polymeric material capable of promoting mineralization of hydroxyapatite, which are useful for fixing prosthetic devices, useful as bone substitutes to directly fill bone defects, to provide substrates for cartilage, and to repair teeth, and methods of making such preparations. The present invention is also directed to a method of treating collagen to provide a micro-structure close to that of native bone.

2. Description of Related Art

The microstructural features of teeth and bone and the processes by which remodeling occurs are of importance in determining desirable microstructures in bone-like substitutes. Because bone substitutes must emulate the function of bone, bone must bond well with them. The nature of this bonding will depend on the pore sizes in the polymeric material capable of forming mineralization of hydroxyapatite. It has been shown that the response of bone to porous implants depends on the pore size. Bone growth occurs in close apposition to an implant which contain 40 $\mu$m pores regardless of whether the implant is a metallic or a ceramic material. For pore sizes of 100 $\mu$m, bone will fill in the pore and for pores sizes in excess of approximately 150 $\mu$m Haversion systems will develop and facilitate the formation of a strong bond with the bone substitute. The ability to directly control microstructural development in a prosthesis composed of a resorbable material and consequently to control its porosity has a major influence on bone intergrowth and prosthesis remodeling. Unfortunately, mechanical integrity and porosity are conflicting functional requirements. Thus, it is unlikely that a single material would be capable of meeting the function requirements of bone. Indeed, none has been found. The alternative is to develop a composite which would exhibit adequate mechanical properties along with the porosity needed to meet the biological requirements for remodeling.

There have been many attempts to prepare a substitute bone material and there are numerous patents disclosing methods of preparation of such substitute bone materials. U.S. Pat. No. 4,440,750 to Glowacki, et al. discloses a plastic dispersion of demineralized bone powder and reconstituted native atelopeptide collagen fibers in a continuous aqueous phase to repair or construct bone by injecting or implanting it at the repair or constructive site. U.S. Pat. No. 4,516,276 to Mittelmeier employs collagen as a fleece described as a grid or network which is than dusted with apatite powder or granules, or the fiber material is mixed with mineral before being formed into layers for implantation into bone. Some patents claim the use of porous hydroxyapatite, for example U.S. Pat. No. 4,629,464 discloses a method for preparation of artificial bone material where sintered microporous hydroxyapatite is used either in a granular or slurried form in a physiological saline solution or in a form of a shaped prosthetic bone substitute. The prepared bone substitute is characterized by an open porous structure. Such an open porous structure allows for ingrowth of natural tissue. Another method and composition of material promoting the growth of bone is disclosed in U.S. Pat. No. 5,073,114. The bone growing composition includes two sizes of hydroxyapatite for supporting the growth of the bone, tetracycline for its antibiotic effect, freeze-dried decalcified human bone for promoting bone growth and fibronectin for promoting connective tissue generation and for gelling the bone growing composition. U.S. Pat. No. 4,776,890 introduces a process for obtaining a matrix of mineral particles in reconstituted atelopeptide collagen comprising reconstituting a mixture of mineral particles with collagen in solution. However, none of the above discussed bone substitutes undergo reaction in vivo which would lead to their exhibiting mechanical properties comparable to those of natural bone.

U.S. Pat. Nos. 4,880,610; 5,047,031; and 5,053,212 to Constantz disclose calcium phosphate compositions useful as cements. The process involves merely mixing two dry ingredients, i.e., a calcium source and a phosphoric acid source to form a kneadable mixture. None of these references disclose or suggest the preparation of polymineralic precursor particles capable of forming hydroxyapatite without additional sources of calcium or phosphate, by reacting a calcium source and a phosphoric acid source in a non-aqueous liquid and then removing the non-aqueous liquid, which can be stored in a dry state and which are stable over long periods of time.

In U.S. Pat. No. 5,053,212, water is liberated in the mechanical mixing of the calcium source with the acidic phosphate source. Disadvantageously, this liberation of water is free to combine with the calcium and acidic phosphate sources which results in calcium phosphates which are slow to react to form HAp, and upon reaction to form HAp again release water, thereby increasing the porosity and limiting the mechanical strength of the resultant product.

W. Brown and Chow, U.S. Pat. No. 4,612,053, disclose mechanically mixing $Ca_4(PO_4)_2O$ with at least one other calcium phosphate selected from the group consisting of $CaHPO_4.2H_2O$, $CaHPO_4$, $Ca_8H_2(PO_4)_4.5H_2O$, (i.e., $Ca_8(HPO_4)_2(PO_4)_4.5H_2O$), $\alpha$-$Ca_3(PO_4)_2$, $\beta$-$Ca_3(PO_4)_2$ and modified $Ca_3(PO_4)_2$ for use in a dental restorative powder, paste and/or slurry. This mechanical mixing does not result in a reaction between $Ca_4(PO_4)_2O$ and the recited calcium phosphates to form polymineralic precursor particles and thus does not disclose or suggest the use of the preparation of polymineralic precursor particles capable of forming hydroxyapatite without additional sources of calcium and phosphate, and which said particles can be stored in a dry state for long periods of time and which when mixed with a polymeric material capable of promoting mineralization of hydroxyapatite, can completely react to form phase-pure hydroxyapatite in vivo within a surgically relevant time of less than 4 hours, particularly less than 2 hours, as in the present invention.

The above discussed patents to W. Brown and Chow and Constanz rely on grinding mixtures of particles to a high fineness, which particles in admixture are then reacted in an aqueous solution to form hydroxyapatite.

Neither U.S. Pat. No. 4,612,053, nor U.S. Pat. Nos. 4,880,610, 5,047,031 or 5,053,212 disclose the preparation of polymineralic precursor particles capable of forming hydroxyapatite which are formed as a result of a chemical reaction between a calcium source and an acidic phosphate source having at least two protons bound to one phosphate in a non-aqueous liquid and wherein said polymineralic precursor particles are comprised of $Ca_x(PO_4)_y$ and unreacted calcium phosphate, and utilizing the same in preparing hydroxyapatite compositions useful as a bone-like substitute or dental composition of the present invention.

The difference between the products of the above discussed patents and the polymineralic precursor particles of hydroxyapatite of the present invention is that each polymineralic particle of the present invention is capable of producing phase pure hydroxyapatite independently and regardless of the presence of any additional additives present in the composition. On the contrary, the compositions of the above described patents utilize physical mixtures of calcium source and acidic phosphate source, i.e., are blends of particles, and additional additives will have an effect on the purity of the HAp produced or on the ability to produce HAp at all.

The present invention is directed to a method of preparation of polymineralic precursor particles capable of forming hydroxyapatite which can be stored over a long period of time, and a composition of hydroxyapatite and polymeric material which is capable of promoting mineralization of hydroxyapatite which, besides exhibiting biocompatibility and the mechanical characteristics required for teeth or artificial bone, can be formed in a surgically relevant time, e.g., usually under 4 hours, particularly under 2 hours. The polymineralic precursor particles of the present invention are formed by chemically reacting a calcium source with the acidic phosphate source to form stable precursor particles which can be stored for long periods of time. No other inventions or publications identified report polymineralic precursor particles capable of forming hydroxyapatite, or a hydroxyapatite composition that can develop bone-like properties in vivo within a surgically relevant time at physiological temperature (body temperature). Further, most of the prior art requires prosthesis preparation in advance of surgery. This complicates treatment and requires taking measurements and separately fitting of the implant. The present invention introduces an novel way of preparing hydroxyapatite at physiological temperature to provide the surgically relevant time of reaction; hydroxyapatite formation is complete within hours, usually within four hours.

The advantages of using the hydroxyapatite composition of the present invention as a bone substitute are that the properties can be tailored to serve a variety of needs. These include development of the microstructures of both cancellous (porous) and cortical (dense) bone. In addition, the proportions of the constituent ingredients can be adjusted accordingly as a means of controlling the rate and extent of remodeling. Remodeling is the term used to describe the process of bone replacement. Remodeling in synthetic bone may be particularly desirable when younger individuals are involved. Remodeling can be achieved when defects are filled with osteoinductive (bone-forming) materials.

The formation of a hydroxyapatite composition of the present invention in vivo is important in a variety of circumstances like gap filling and bone fragment stabilization. A synthetic material to fill bone defects that is compatible with decalcified bone has not been before identified and there has been a long felt need in the art. The initiation of any bone remodeling procedure will occur more rapidly if a hydroxyapatite-based prosthesis can be placed into close or microscopic apposition with bone. As a result of the present invention, the present method is amenable to placement of a bone-like composition of the reactants into close apposition with bone. This would eliminate the existence of a macroscopic gap between a synthetic hydroxyapatite-based prosthesis and bone or to fill gaps between a metallic prosthesis and bone. The development of union would be promoted in both instances, as a result of the present invention.

SUMMARY OF THE INVENTION

The present invention provides a composition which comprises polymineralic precursor particles capable of expeditiously forming phase pure hydroxyapatite at physiological temperatures without additional calcium or phosphate. The composition can be used in preparing a bone-like substitute or for filling teeth. The composition forms phase pure hydroxyapatite upon setting in a clinically relevant time in vivo while being biocompatible and possessing mechanical properties in the range of those exhibited by natural bone and teeth. The synthetic bone-like composition is also conducive to the rapid ingrowth of bone.

In summary, the present invention is directed to a composition which comprises i.) as a solids component
  (A) polymineralic precursor particles of hydroxyapatite prepared by reacting (a) a calcium source, with (b) an acidic phosphate source having at least two protons attached to one phosphate, in (c) a non-aqueous liquid and removing said non-aqueous liquid; said produced polymineralic precursor particles capable of forming phase pure hydroxyapatite having a Ca/P ratio of from 1.5 to 1.67; and
  (B) a polymeric material which is capable of promoting mineralization of hydroxyapatite from said polymineralic precursor particles (A) and wherein the weight ratio of (A)/(B) is from 100/0 to 40/60, respectively: and (ii.) a physiologically acceptable aqueous liquid;

said aqueous composition having a liquid-to-total solids weight ratio of 0.15 to 1.5:

and wherein said aqueous composition reacts to form phase pure hydroxyapatite from component (A) at physiological temperatures within 4 hours, and a method of making said composition.

Another object of the present invention is to provide physiologically useful hydroxyapatite composition comprising hydroxyapatite and optionally a polymeric material capable of promoting mineralization of hydroxyapatite, for repairing teeth or for bone grafting and implantation, wherein said composition meets the requirements of a bone-like material and which cure to form phase-pure hydroxyapatite in a surgically relevant time, preferably under four hours.

Another object of the present invention is to provide a method of filling in any bone defects with, or implanting a biocompatible and structurally strong, easily formed synthetic bone-like composition into a body.

A further object of the invention is to provide a method of making polymineralic precursor particles capable of forming hydroxyapatite without additional sources of calcium or phosphate which have a long storage life, and which can be premixed with a polymeric material capable of promoting mineralization of hydroxyapatite prior to use in a body which comprises:

(a) reacting at least one calcium source, with at least one acid phosphate source having at least 2 protons attached to one phosphate, in a non-aqueous liquid for a time sufficient to form said polymineralic precursors particles and having a Ca/P ratio of 1.5 to 1.67; and (b) collecting said polymineralic precursor particles.

A further object of the invention is a method of treating insoluble collagen suitable for use in a synthetic bone-like composition which comprises:

(a) suspending insoluble collagen in an acidic solution to form a suspension;

(b) subjecting said suspension to a mechanical action;

(c) freezing said suspension;

(d) thawing said frozen suspension; and (e) collecting said treated collagen.

Still a further object of the invention is to provide a kit comprising a container of polymineralic precursor particles capable of forming hydroxyapatite, which can be stored over long periods of time; and which can be utilized for the preparation of the hydroxyapatite composition for a dental or surgical procedure which will benefit from using said hydroxyapatite composition.

This and other objects and advantages of this invention are described and are particularly delineated in the appended claims.

DETAILED DESCRIPTION OF THE PREFERRED EMBODIMENTS

One embodiment of the present invention is directed to a method of producing polymineralic precursor particles capable of forming hydroxyapatite in the absence of additional sources of calcium and phosphate, which comprises the steps of:

(a) reacting at least one calcium source, with at least one acid phosphate source having at least 2 protons attached to one phosphate, in a non-aqueous liquid for a time sufficient to form said polymineralic precursors particles comprising $Ca_x(PO_4)_y$ and unreacted calcium source said polymineralic precursor particles having an overall Ca/P ratio of 1.5 to 1.67; and (b) collecting said polymineralic precursor particles.

While not being bound to any theories, important advantages of preparing the polymineralic precursor particles capable, of forming hydroxyapatite, of the present invention in a non-aqueous liquid are the following. A non-aqueous liquid lowers the activity of water to the point that free water liberated in the formation of polymineralic precursor particles does not react further and is therefore removed from the system.

After the reaction which forms the polymineralic precursor particles is completed, the non-aqueous liquid is removed from the precursor particles by, e.g., filtration. Additional washing with a non-aqueous liquid removes any residual free water which prevents any further reacting between the hydroxyapatite precursors. The process of the final liquid removal is by evaporation. The products produced as a result of this reaction are polymineralic particles comprising $Ca_x(PO_4)_y$ and unreacted calcium phosphate, e.g., tetracalcium phosphate $Ca_4(PO_4)_2O$ (abbreviated as $C_4P$) when $C_4P$ is used as the calcium source. Included in the formula $Ca_x(PO_4)_y$ are salts of the formula comprising $Ca_x(PO_4)_y$. It is contemplated that depending on the calcium source or acidic phosphate source or the temperature at which the reaction is conducted condensed calcium phosphates e.g., $P_2O_5$ and $P_2O_7$ can form in said polymineralic precursor particles. Specifically, none of the solids formed according to the method of the present invention contain water of hydration, as do $CaHPO_4.2H_2O$ or $Ca(H_2PO_4)_2.H_2O$. In addition, no monobasic phosphate species, $H_2PO_4$ as in $Ca(H_2PO_4)_2$ remain. Both these conditions are required for the storage of the polymineralic precursor particles of the present invention.

By way of explanation of the prior art, all acidic calcium phosphates and $Ca_4(PO_4)_2$ dissolve incongruently. This means that when a crystal of $CaHPO_4$ or $Ca(H_2PO_4)_2.H_2O$ dissolves, it creates a solution which is supersaturated in another calcium phosphate before the solution becomes saturated with respect to the dissolving crystal (see FIG. 1). This means that the other calcium phosphate precipitates on the surface of the dissolving crystal. For $CaHPO_4$, $CaHPO_4.2H_2O$ and for $Ca_4(PO_4)_2O$, the other calcium phosphate is hydroxyapatite. For $Ca(H_2PO_4)_2.H_2O$, the other calcium phosphate is $CaHPO_4.2H_2O$. Therefore, when these calcium phosphates are used as reactants for hydroxyapatite, their dissolution causes hydroxyapatite to form on their surfaces, reduces the effective surface area for dissolution, and slows down reaction.

However, when the individual polymineralic particles are comprised of $Ca_x(PO_4)_y$ and unreacted calcium phosphate as in the present invention, this effect is precluded. Such polymineralic precursor particles cannot be formed by intergrinding or mixing, they must be formed by reacting a calcium source and an acidic phosphate source having at least two protons attached to one phosphate in a non-aqueous liquid. Since the produced polymineralic precursor particles do not contain water molecules or protons in the form of $H_2PO_4$, which could initiate further reactivity, these precursor particles can be stored for an unlimited period of time, if kept dry. The extended shelf-life of such a product contributes to its advantage as a dental or bone-like substitute which can be constituted in an operating theater in a surgically relevant timeframe. Comparison of the reactivities of a freshly prepared preparation with one which had been stored for approximately one year showed was negligible with respect to the rate of hydroxyapatite formation.

The polymineralic precursor particles of the present invention can be further mixed with a polymeric material which acts as a substrate for hydroxyapatite mineralization and can be further sterilized by heat, by gamma radiation or by ethylene oxide.

Formation of hydroxyapatite in vivo from the polymineralic precursors of the present invention allows the reactants to be placed in an intimate association with the bone or tooth being repaired. This cannot be achieved by using preformed hydroxyapatite prosthesis.

Another embodiment of the present invention is directed to a method of treating collagen suitable for use as a second constituent in a hydroxyapatite composition which imitates natural bone, and which has pore sizes ranging from 2 μm to 100 μm.

Collagen is commercially obtained in two basic forms; (1) solubilized individual fibrils ("soluble collagen") and (2) coarse granules of ground protein. Neither of these two readily available forms are useful in forming an intimately mixed composite exhibiting the mechanical properties that would be desirable in a bone substitute. Solubilized collagen fibrils are difficult to obtain in a useful concentration range. More importantly, mechanisms to covalently crosslink the fibrils under conditions compatible with those in vivo do not appear to have been identified. Conventional cross linking agents, such as dialdehydes, are not biocompatible and, thus, not useful. On the other hand, coarse granules of ground collagen are too large to be used in the development of an intimately mixed microcomposite. The granules are of a size whereby their incorporation into a composite would actually cause a reduction in mechanical properties by creating defects.

Figure 3:
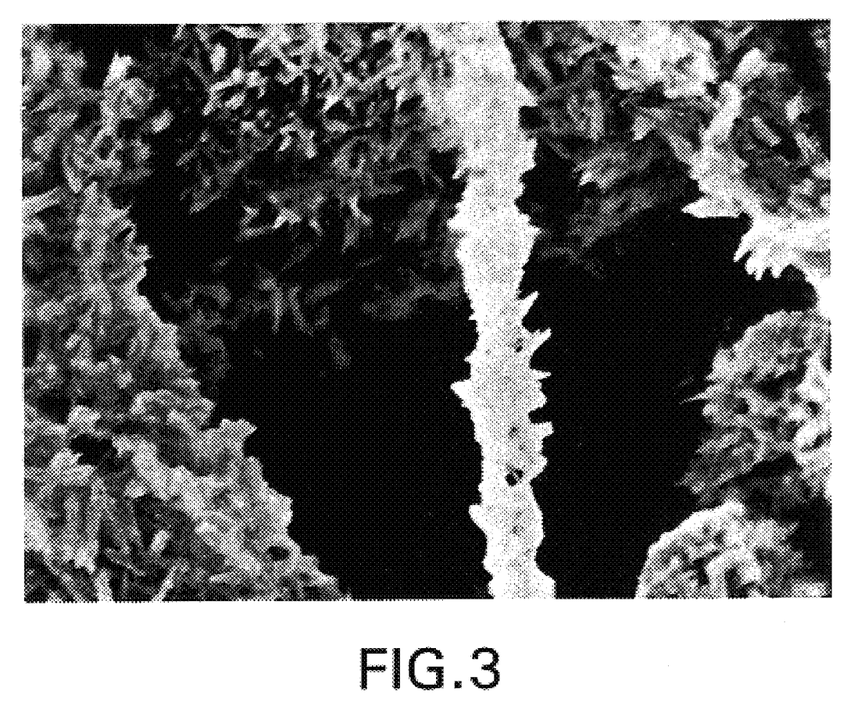
FIG. 3 is mineralized collagen network where the original porosity present is retained.

The present invention is also directed to a novel method of preparation of collagen suitable for developing a synthetic bone material comprising several steps. The collagen produced in this way forms a three dimensional tennis-net like structure (FIG. 4) which provides the spaces adequate for rapid transport of reagents to mineralization sites hydroxyapatite on the individual collagen fibers (FIG. 3).

Hydroxyapatite Formation—As an example of using polymineralic precursor particles of the present invention, calcium deficient hydroxyapatite (having a Ca/P ratio of 1.5) can be formed from polymineralic precursor particles by the following reaction:

[EQ. 1]

wherein $ax+4b=9n$ and $ay+2b=6n$.

The $Ca_x(PO_4)_y$ of variable composition forms by reaction of a calcium source and an acidic phosphate source as described herein below in a non-aqueous liquid in which e.g., when $Ca_4(PO_4)_2O$ is used as the calcium source, $Ca_4(PO_4)_2O$ is also partially simultaneously consumed. $Ca_x(PO_4)_y$ may also contain an indeterminate number of protons. $Ca_x(PO_4)_y$ may exhibit a range of Ca to P ratios of less than 1.67 and particularly a ratio of about 1.

In the reaction of the calcium source with the acidic phosphate source, the molar ratio or amount of calcium source to acidic phosphate source employed is not critical so long as the overall Ca/P ratio in the produced polymineralic precursor particles is in the range of 1.5 to 1.67 and can be ascertained by one skilled in the art.

To prepare the polymineralic precursor particles capable of forming hydroxyapatite of the present invention the reaction must take place in a non-aqueous liquid. Preferably the non-aqueous liquid is of sufficient volatility so as to be easily removed by evaporation after the formation of the polymineralic precursor particles. The non-aqueous liquid is not a solvent for said calcium source or acidic phosphate source, but rather blocks the reaction of water liberated during the formation of the polymineralic particles of HAp. At the same time, the non-aqueous liquid prevents the water which is liberated from reacting with the produced polymineralic precursor particles of HAp. Moreover, the non-aqueous liquid does not react directly with the calcium and acidic phosphate sources. When it is desired to produce only hydroxyapatite complete at reaction, the proportions of the calcium source to the acidic phosphate source is to be selected to achieve Ca/P ratios from 1.5 to 1.67.

The amount of non-aqueous liquid used in preparing the polymineralic precursor particles of the present invention is not critical. An amount of 1 volume of reactants to 2 volumes of non-aqueous liquid may be used as a guideline. Moreover, the non-aqueous liquid does not have to be non-toxic since the non-aqueous liquid is completely removed from the polymineralic precursor particles prior to use in vivo.

Examples of such non-aqueous liquids include, but are not limited to, liquid aliphatic hydrocarbons which may be straight, branched or cyclic, and aromatic hydrocarbons which may be further substituted with functional groups such as halogens. Examples of liquid aliphatic hydrocarbons, include, but are not limited to substituted or unsubstituted liquid alkanes, and liquid alkenes. Examples include but are not limited to butane, pentane, hexane, heptane, $CCl_4$, $CH_2Cl_2$ and $C_2Cl_6$.

The temperature range for reacting the calcium source with the acidic phosphate source is not critical, so long as the temperature is below the boiling point of the non-aqueous liquid employed. As the temperature increases the likelihood of the production of condensed phosphates, e.g., $(P_2O_5)$ and $P_2O_7$ also increase in the produced polymineralic precursor particles of the present invention and fall within the scope of the polymineralic precursor particle composition.

The particle size of the produced polymineralic precursor particles are in the range of from 0.5 μm to 500 μm, preferably 2 to 10 μm and more preferably 2 to 5 μm.

Examples of calcium sources include calcium oxide, calcium carbonate, calcium hydroxide, calcium hydroxide-calcium carbonate double salts, or a basic calcium phosphate having a Ca/P ratio greater than 1.67 or mixtures thereof.

Depending on the type of hydroxyapatite desired, the calcium sources used in preparing the polymineralic precursor particles may be selected to form, for example, calcium deficient hydroxyapatite, $Ca_9HPO_4(PO_4)_5OH$, stoichiometric hydroxyapatite, $Ca_{10}(PO_4)_6(OH)_2$, or any intermediate composition, and are well within the level of skill in the art.

Examples of acidic phosphate sources having at least two protons attached to one phosphate is selected form the group consisting of $H_3PO_4$, $H_3PO_4 \cdot \frac{1}{4}H_2O$, $Ca(H_2PO_4)_2$, $Ca(H_2PO_4)_2 \cdot H_2O$ and $NH_4H_2(PO_4)_2 \cdot nH_2O$ or mixtures thereof.

Figure 1:
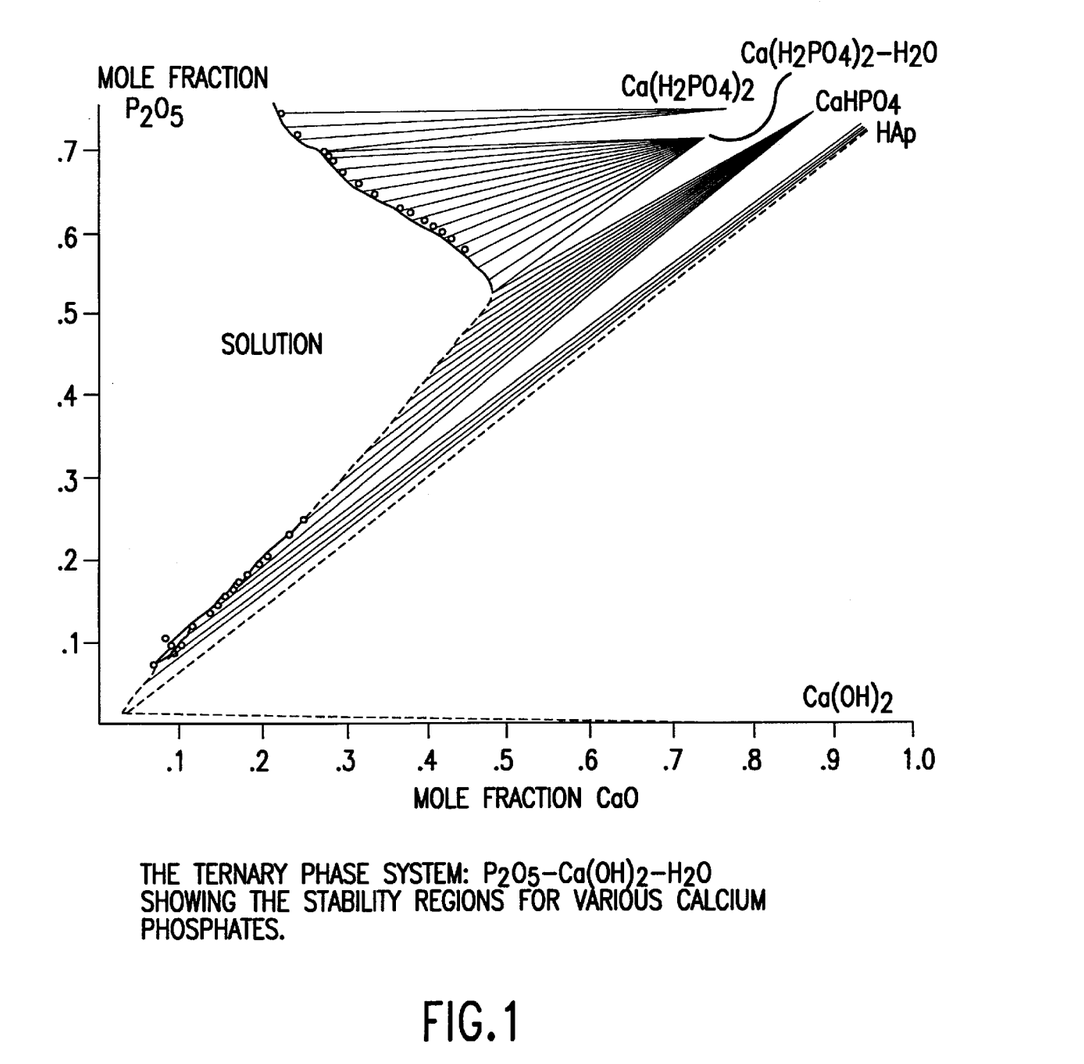
FIG. 1 is a phase diagram.

The present invention uses a non-aqueous liquid for reaction of the calcium source with the acidic phosphate source which is rationalized in the phase diagram of FIG. 1. This diagram shows the compositional relationships among the calcium phosphates to be peritectic reactions. As a result, the reaction of acidic and basic calcium phosphates results in the acidic phosphates being overgrown by hydroxyapatite or intermediate products and causing the complete reaction to hydroxyapatite to become diffusionally controlled. For example, the hydrolysis of $CaHPO_4$ occurs as follows:

EQ [2]

even in the presence of $Ca_4(PO_4)_2O$. The hydroxyapatite formed does so as a coating on the $CaHPO_4$ reactant and results in a lengthy period of time to complete reaction.

Reaction is more extensive if the initial reactant is $Ca(H_2PO_4)_2 \cdot H_2O$ but the reaction of this with $Ca_4(PO_4)_2O$ or with a mixture of $Ca_4(PO_4)_2O$ and $Ca(OH)_2$ at physiological temperature results in the formation of an intermediate product $CaHPO_4 \cdot 2H_2O$. This intermediate hydrolyzes in the same way as the $CaHPO_4$ described in EQ. [2].

According to the present invention reaction of various sources of calcium and/or phosphate with $Ca_4(PO_4)_2O$ in a non-aqueous liquid results in the formation of polymineralic precursor particles of $Ca_x(PO_4)_y$ and $Ca_4(PO_4)_2O$. When mixed with a physiologically acceptable liquid such as sterile water for injection, or normal saline for injection, these combinations of reactants react completely to form hydroxyapatite within minutes to a few hours without the formation of intermediates.

On the contrary, mixing of $Ca_4(PO_4)_2O$ with $H_3PO_4$, or $H_3PO_4 \cdot \frac{1}{4}H_2O$ with $Ca(H_2PO_4)_2 \cdot H_2O$ or $Ca(H_2PO_4)_2$ results formation of intermediates. In particular, $CaHPO_4 \cdot 2H_2O$ tends to form. Such formation precludes the mixing of such hydroxyapatite precursors prior to the time at which they could be placed in vivo. Reaction of such precursors in water forms a hardened mass of $CaHPO_4 \cdot 2H_2O$ and unreacted $Ca_4(PO_4)_2O$ which require a lengthy period for complete reaction to hydroxyapatite.

The type of reaction vessel or its size for preparing the polymineralic precursor particles of the present invention is not critical, and can be any vessel capable of holding the calcium source, acidic phosphate source and non-aqueous liquid in admixture so as to allow the reaction to take place. An example of such a vessel is any commercially available polyethylene bottle. Inert pellets can be added to the reaction vessel in order to prevent agglomeration of the reactants as well as the produced polymineralic precursor particles. Examples of such pellets to prevent agglomeration, include but are not limited to, zirconia, alumina and polycarbonate pellets.

The reaction for producing the polymineralic precursor particles occurs when the calcium source and the acidic phosphate come into contact with each other, and can be facilitated by agitation, rolling or stirring.

The process of the present invention was developed because mechanical mixtures of particles of, e.g., $CaHPO_4$ and $Ca_4(PO_4)_2O$ or $CaHPO_4 \cdot 2H_2O$ and $Ca_4(PO_4)_2O$ in suitable proportions, to form hydroxyapatite as shown in U.S. Pat. No. 4,612,053 to W. Brown and Chow requires an extended period of time to reach completion while those of $Ca(H_2PO_4)_2 \cdot H_2O$, $H_3PO_4$ or $H_3PO_4 \cdot \frac{1}{2}H_2O$ with $Ca_4(PO_4)_2O$ form intermediates which may also persist for lengthy periods, which is undesirable in the average time for a dental or surgical procedure.

Figure 4:
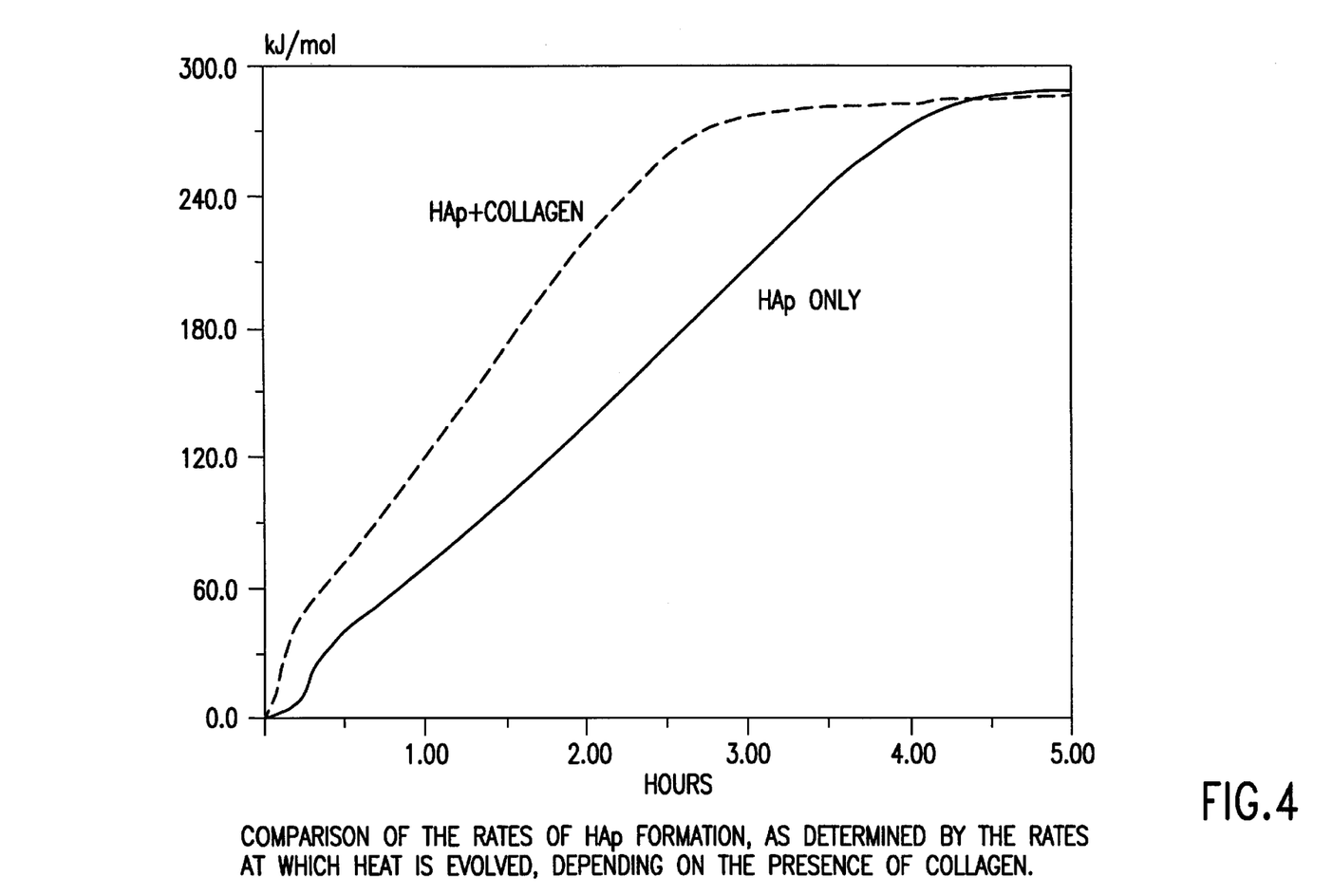
FIG. 4 are curves comparing the heat liberated during the formation of hydroxyapatite according to EQ 1 depending on the presence of a collagen network. Three hydroxyapatite:collagen volume ratios are shown: 10, 5, 2.

Collagen Treatment Process—The collagen treatment method of the present invention serves three functions in contributing to the development of hydroxyapatite-collagen bone replacement composites. It allows coarse collagen granules to be converted into fibrils. It orients these fibrils in a three dimensionally interconnected network (FIG. 4). This network structure provides a template on which hydroxyapatite formation occurs (FIG. 3). Thus, the treated collagen prepared by the process of the present invention also serves to facilitate hydroxyapatite formation in vivo.

The collagen treatment method of the present invention is achieved by a combination of physical, chemical and mechanical actions. Granular insoluble collagen obtained from, e.g., Sigma Chemical Company, is suspended in an acidic solution and the collagen subjected to a mechanical action, such as from a commercial blender (step a). The organic acid breaks the hydrogen bonds between fibrils and allows their expansion in solution by hydration. The acid may also be selected to control the rate of hydroxyapatite formation (discussed below). Mechanical shear promotes the physical separation and expansion of the fibrils. After this processing step, the suspension is rapidly frozen in liquid nitrogen (step b). Freezing in other low boiling point liquids (He, $H_2$, $O_2$, Ar, etc., or solids ($CO_2$) will also work. Expansion of water present on freezing this suspension assists in the expansion and separation of the dense tendinous collagen structure. The frozen mass is then thawed and mechanically sheared for a second time to further the separation of the fibrils (step c). This process can be repeated as many times as is necessary.

Figure 2:
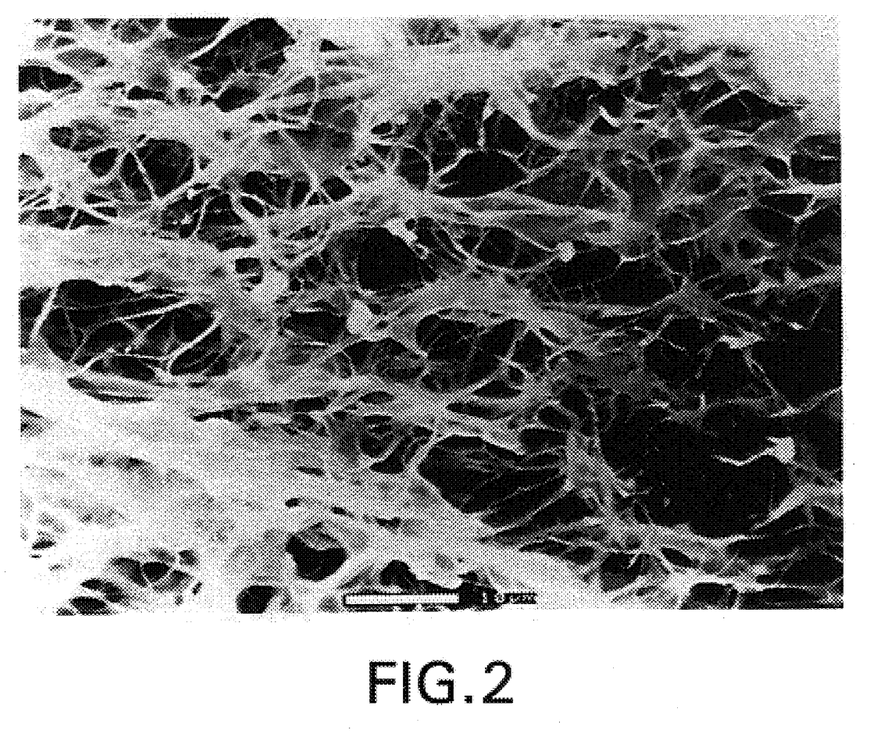
FIG. 2 is a microstructure of the collagen network of the present invention after the collagen has been processed.

After reblending, the suspension is again frozen using liquid nitrogen and then freeze-dried. Freeze drying allows the removal of both the water and the organic acid. This process results in a three dimensional organic matrix consisting of oriented submicron fibrils interconnected with fibrils and collagenous membranes. This matrix is a result of the freezing direction, namely the fibrils align in the direction of the solidification front. The extended structure provides a network for the formation of hydroxyapatite. This structure has pores and channels ideal for the incorporation of the hydroxyapatite as can be seen in FIG. 2. In addition, the pore and channel dimensions can be easily controlled by altering the acid concentration and water content in step (a). Thus, altering the acid concentration and water content to control the collagen microstructure can also control the resulting properties of the synthetic bone. The treated collagen of the present invention has pore diameters in the range of from 2 $\mu$m to 100 $\mu$m.

A number of innovative features are associated with the present inventive method of treating insoluble collagen. First, the insoluble collagen can be processed quite rapidly. Insoluble collagen harvested by known surgical methods from another part of the individual to be treated can be used as a result. Collagen obtained from another individual can also be treated according to the present process.

When the hydroxyapatite produced according to the present invention is used to repair dentitia, the polymineralic precursor particles capable of forming hydroxyapatite can be used alone, or additional components can be added to alter the physical properties of the hydroxyapatite.

When the composition of the present invention is used as a synthetic bone-like HAp composition, polymeric materials capable of allowing mineralization of hydroxyapatite can be added in an amount sufficient to achieve any of a number of desired effects. Such desired effects can be, e.g., bone formation, enhanced resorption, growth of osteoblasts and/or osteoclasts, angiogenesis, cell entry and proliferation, mineralization, altering mechanical properties, or the like.

In defining the composition, by solids component is meant the total weight of (A) the polymineralic precursor particles of hydroxyapatite; or the total weight of (A) plus the polymeric material capable of promoting mineralization of hydroxyapatite (B).

The weight ratio of (A) to (B) is in the range of 100/0 to 40/60 respectively, particularly 99.99/0.01 to 60/40 respectively, and more particularly 99/1 to 60/40 respectively, depending on the polymeric material employed. When the polymeric material is bone associated protein, and particularly treated insoluble collagen, the weight ratio of (A)/(B) is 99/1 to 60/40.

By liquid-to-total solids weight ratio is meant the ratio of the total weight of the physiologically acceptable aqueous liquid to the total weight of the solids present in the composition. The total weight of the solids will include the solids component described in the preceding paragraph as well as any additional additives, such as fillers, bisphosponates, etc.

The physiologically acceptable aqueous liquid which is used to constitute formation of phase pure hydroxyapatite in vivo will be substantially pure, e.g., sterile water for injection, normal saline for injection or equivalents thereof.

Examples of such polymeric materials (B) can be synthetic polymers, or proteins known to be associated with bone, cartilage, or dentin.

With respect to synthetic polymeric materials those which contain functional groups capable of being hydrolyzed by $H_2O$, such as carboxyl, amine or sulfonate groups, are useful so long as the functional groups on the polymer are capable of forming salt bridges with calcium and phosphate. Examples of water soluble synthetic polymers, include but are not limited to polyacrylic acid and polyacrylic-itaconic acid co-polymers.

Examples of such polymeric bone proteins include collagen, particularly Type 1, osteonectin ZHS-glycoproteins, sialoproteins (BSP), bone-Gla-protein (BGP) matrix-Gla-protein bone proteoglycan bone phophoglycoprotein, bone phospho-protein, skeletal growth factor, and the like.

Examples of such polymeric cartilage proteins include chondrocalcining proteins.

Examples of such polymeric dentin or enamel proteins include glycoproteins such as Gla protein, phosphophoryn, amelogelnin, and enamelin.

Other materials may be added to the composition of the present invention to provide for specific types of mechanical physical properties. Both inorganic and organic fibrous materials can be employed. Examples include hydroxyapatite fibers and biodegradable organic fibers such as polyglycolic acid.

Fillers can be mixed with the polymineralic precursor particles of the invention and optionally polymeric materials, prior to reaction with physiologically acceptable aqueous liquid, in order to control the porosity, and increase the early strength of the compositions during mixing and surgery. Examples of filler include preexisting HAp, $CaHPO_4$, $CaHPO_4$ coated with fluorapatite, $Ca_4(PO_4)_2O$ coated with $CaHPO_4$. The filler can be formulated to any particle size, preferably between 15 to 75 $\mu$m. The proportion of filler, when present, can be as high as 65 wt % based on the weight of the solids component (A) and (B) of the composition.

Further, additional additives can be added which include, but are not limited to fluoride sources, antibiotics, surfactants, and dispersants in order to exert their intended effect.

With respect to the addition of antibiotic, the choice of antibiotic incorporated into the composition depends on the microorganisms to be treated, and is well within the level of skill in the art.

Effective amounts of antibiotics can be incorporated into the compositions in order to prevent or treat infections of the bone or dentitia or infections of surrounding tissue. Effective amounts are well known or can be readily ascertained by one skilled in the art.

Examples of antibiotics include, but are not limited to penicillin, cephalothin, tobramycin, gentamycin, nafcillin, rifampin, clindamycin, polymyxin, metronidazole, chloramphenicol well known in the art as evidenced by the Physicians Desk Reference, 48th Edition, 1994.

Effective amounts of the antibiotics can be dissolved in the physiologically acceptable liquid or can be mixed with the polymeric precursor particles of HAp and optionally the polymeric material. The rate of release of antibiotics can be controlled by controlling the initial concentration of the antibiotic.

The hydroxyapatite tooth and bone substitute composition of the present invention can be prepared by a number of methods.

In a first method, the polymeric material capable of promoting mineralization of hydroxyapatite can be added directly into the non-aqueous liquid used in forming the polymineralic particle precursors of HAp, prior to removal of the non-aqueous liquid.

In a second method, the polymineralic precursors of HAp may be mixed with a polymeric material capable of promoting mineralization of hydroxyapatite in an aqueous phase, prior to use in vivo.

When preparing the composition of the present invention, the liquid-to-total solids weight ratio is from 0.15 to 1.5 (liquid-to-total solids component), preferably 0.25 to 1.0.

When preparing a pure HAp composition with no polymeric material, the ratio of the liquids-to-total solids (in this instance the total solids is precursor particles of HAp) is directly related to the compressive strength of the phase pure HAp resultant product. When the liquid to precursor particle of HAp weight ratio is approximately 0.25, a compressive strength of the resultant HAp product of up to 175 MPa is achieved.

The additives can be added at any time during the process of preparing the composition, up until use of the composition in vivo in the relevant procedure.

Regardless of which method is used, the resultant composition can be utilized in mass as a monolith or can be manipulated with a polymeric material, such as collagen, to achieve a net anisotropic orientation.

In preparing the composition of the present invention for use in vivo, if the first method is used, the non-aqueous liquid is removed by evaporating at ambient temperature. If the second method is used, blend of the polymineralic precursors of HAp, and polymeric material in aqueous phase is frozen in liquid nitrogen and then freeze dried. After the non-aqueous liquid or the frozen water is removed, the resulting blend is crushed lightly to yield a slightly fibrous powder. This powder can then be sterilized and stored dry ready for constitution during the relevant procedure. When needed, it can be hand or mechanically mixed with 150% of its weight of a physiologically acceptable liquid, such as sterile water for injection, or normal saline. This mixing step occurs prior to anticipation of use in vivo.

Compositional Adjustments—Sodium and carbonate can be incorporated into the hydroxyapatite compositions by carrying out the reaction of $Ca_4(PO_4)_2O$ and $Ca_x(PO_4)_y$ described above in the presence of up to 7% by weight of particulate $NaHCO_3$, based on the weight of the polymineralic precursor particles of HAp, to obtain a composition which is as close as possible to natural bone and/or teeth. The incorporation of carbonate and sodium into the hydroxyapatite composition demonstrates that the $Na^+$ and $CO^2{}_{3-}$ concentrations in solution decreased linearly as the formation of hydroxyapatite proceeds, attaining concentrations of a few millimoles at complete reaction. Use of 7% by weight of $NaHCO_3$ based on the weight of the precursor particles of HAp resulted in a hydroxyapatite composition containing approximately 3.6 wt % $CO_3$. As a result of incorporating up to 7% by weight of Na and carbonate and particularly, 1 to 7% by weight of Na and carbonate, a hydroxyapatite composition close to that of native bone can be formed by a reaction which is physiologically compatible in vivo. Therefore, a mineral phase close in composition to that of natural bone and teeth can be formed in vivo. Developing prostheses which will remodel in vivo in a manner similar to that of natural bone and teeth.

Figure 5A:
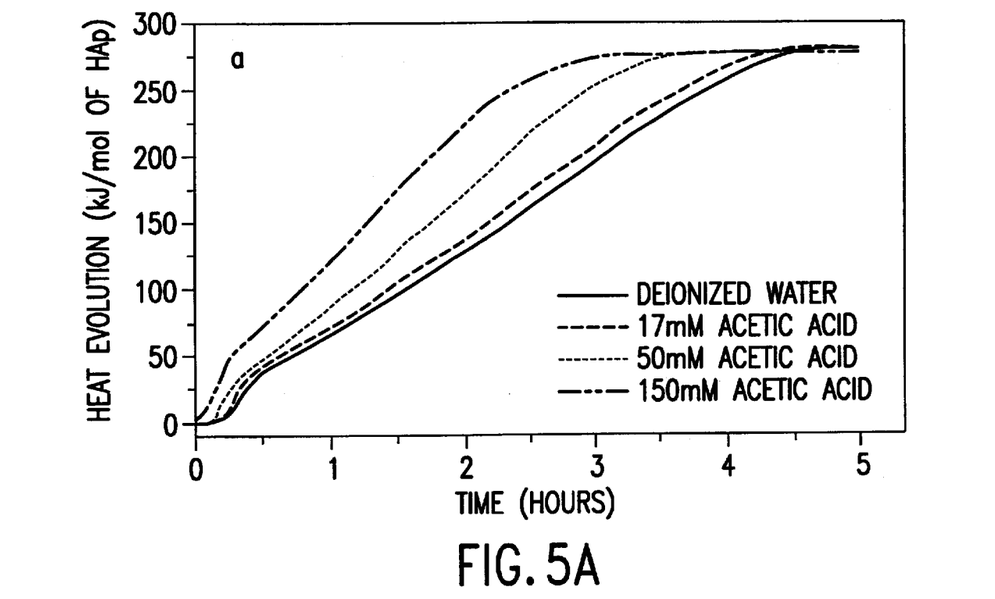
FIGS. 5A and 5B show effects of citric and acetic acids on the reaction to form hydroxyapatite.
Figure 5B:
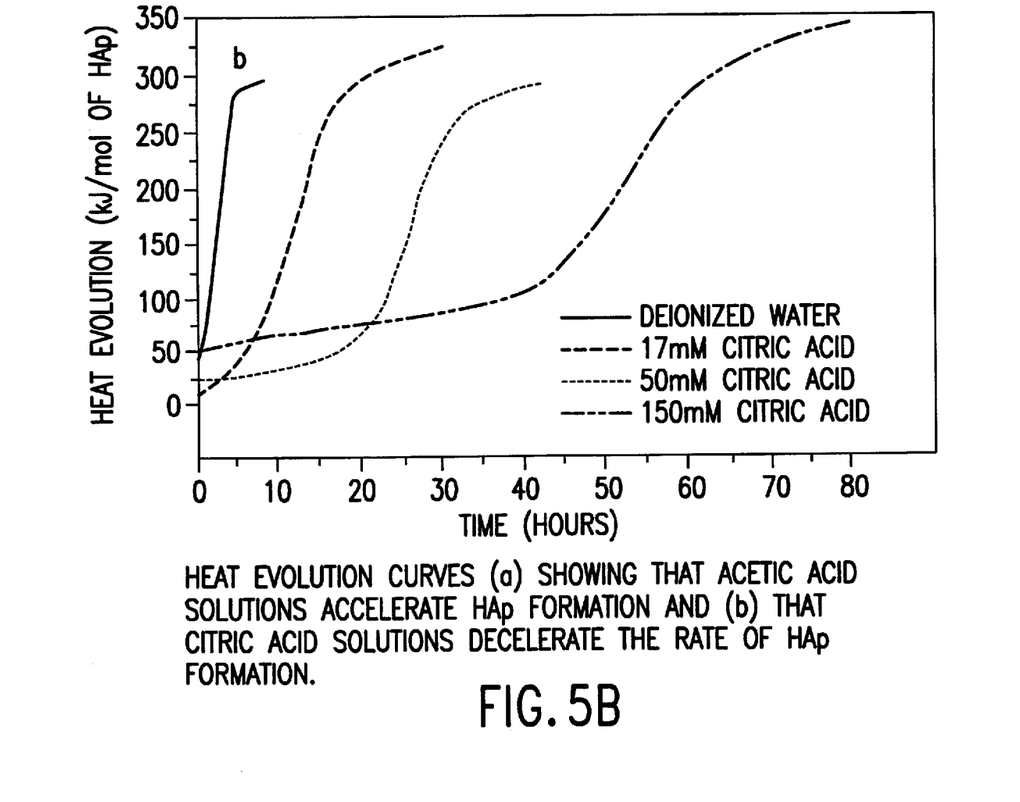

A variety of hydroxyapatite compositions may be achieved, depending on desired application of the dentist or surgeon. Alkali phosphates can be added to the aqueous solution to influence the kinetics of reactant dissolution, for example by making such dissolution increasingly congruent. A fluoride source, for example, NaF or $CaF_2$, can be added to form fluoride substituted apatite in which can be present to partially or completely substitute for OH. Moreover, various acids, e.g., acetic acid and citric acid can be added to the aqueous phase, which do not enter the apatite structure, but which influence the rate of hydroxyapatite formation. Specifically, small additions, e.g., (from 15 to 150 mM) of acetic acid to the aqueous phase accelerate the onset of hydroxyapatite formation from 20 minutes to 5 minutes, while small additions of citric acid (from 15 to 150 mM) delay the onset of hydroxyapatite formation from 5 to 45 hours (FIGS. 5A and 5B). Such additives provide the means to control the rate of hydroxyapatite formation in vivo. The presence of such additives may be synergistically associated with the presence of the processed collagen (as discussed).

Having generally described the invention, the following specific examples are included for the purpose of illustration only and not intended to limit the scope of the invention. For ease of calculation, the liquid components in the following examples are rounded off to have a density of 1.0 g/ml. All liquid-to-total solids ratios are by weight.

EXAMPLE 1

Preparation of Polymineralic Precursor Particles Capable of Forming HAP Having a Ca/P Ratio of 1.5

In a typical run to prepare polymineralic particle precursors of hydroxyapatite which will be employed to form $Ca_9HPO_4(PO_4)_5OH$ in vivo, 127 g of $Ca(H_2PO_4)H_2O$ are reacted with 366 g of $Ca_4(PO_4)_2O$. The $Ca_4(PO_4)_2O$ is prepared by firing an intimate mixture of equimolar amounts of $CaCO_3$ and $CaHPO_4$ powders to 1400° C. for 4 hours. After cooling the $Ca_4(PO_4)_2O$ is ground to an average particle size of 2–5 μm using standard powder preparation techniques. This material is then reacted with the acidic phosphate source $Ca(H_2PO_4).H_2O$, which is commercially available, by placing it and $Ca_4(PO_4)_2O$ in a 1-liter polyethylene bottle with approximately 400 ml of heptane.

Approximately 250 g of zirconia or alumina, or 100 g polycarbonate pellets are added and the bottle is sealed. The presence of the pellets limits agglomeration. This bottle is then placed in any shaking or rolling device. In the reaction, all of the $Ca(H_2PO_4).H_2O$ and some of the $Ca_4(PO_4)_2O$ are consumed in the formation of the polymineralic precursor particles comprising $Ca_4(PO_4)_2O$ and $Ca_x(PO_4)_y$. These produced polymineralic particles can then react rapidly in the presence of water to form hydroxyapatite in vivo.

There is a negligible reduction in particle size during reaction in heptane; therefore, this processing step does not involve grinding. The high reactivities of the reactants formed according to the present process cannot be duplicated by grinding in air, grinding in aqueous solvents, or grinding in water. After reaction, the slurry of polymineralic particles and the pellets is placed on a filter funnel and the bulk of the heptane is removed by vacuum suction and can be reused after distillation. The pellets are then removed by hand picking. Any material which adheres to pellets is removed by washing in heptane. Heptane not removed by vacuum suction is allowed to evaporate, either at room or slightly elevated temperature. Evaporation may also be carried out in vacuum.

As described above, $Ca_4(PO_4)_2O$ is prepared by solid state reaction at elevated temperature and then crushed to an average particle size of from 2–5 microns. Attempts to intergrind $Ca_4(PO_4)_2O$ with $CaHPO_4$ or with $CaHPO_4.2H_2O$, or with $Ca(H_2PO_4)_2.H_2O$, or with $Ca(H_2PO_4)_2$ did not result in an assemblage of reactants which were as reactive as the polymineralic precursor particles prepared in heptane. When used with the treated collagen of the present invention, it is the polymineralic particles of the calcium phosphate reactants, which form hydroxyapatite in aqueous solution, which are constituted in a manner to achieve very rapid reaction as set forth in FIG. 4. When reacted with water at physiological temperature, reactions of the polymineralic particles achieve a substantial degree of completion in one hour or less and convert completely to hydroxyapatite in periods of time which range from about 30 minutes to 4 hours.

EXAMPLE 2

Preparation of Mixed Calcium Sources

Calcium sources composed of a mixture of $Ca_4(PO_4)_2O$ and CaO or of $Ca_4(PO_4)_2O$ and $Ca_3(PO_4)_2$ are prepared at high temperature by processing similar to that described in Example 1, above. This is accomplished by varying the proportions of calcium-containing and phosphate-containing reactants. Mixtures composed of $Ca_4(PO_4)_2O$ and CaO require Ca/P ratios greater than 2 while mixtures of $Ca_4(PO_4)_2O$ and $Ca_3(PO_4)_2$ require ratios less than 2. Mixtures of $Ca_4(PO_4)_2O$ and $Ca_{10}(PO_4)_6O$ (oxyapatite) are prepared when the reaction temperature is maintained below about 1275° C. When the high temperature reaction time is shorter than about 4 hours and when the reaction temperature is below about 1300° C., mixtures of $Ca_4(PO_4)_2O$, and $Ca_{10}(PO_4)_6O$ are prepared. Non-equilibrium mixtures of CaO and $Ca_3(PO_4)_2$ are produced if the reaction temperature is above about 1600° C., which is high enough to attain a liquid phase. High temperature reactions in the presence of water vapor and/or $CO_2$ results in the formation of mixtures of CaO, $Ca(OH)_2$, and $CaCO_3$ and calcium hydroxide—calcium carbonate double salts.

Polymineralic particles are prepared from these calcium sources by reacting them with the above described acidic phosphates in a similar fashion as set forth in example 1. Of course, the proportions of the reactants must be adjusted to ensure that the polymineralic particles formed have a Ca/P ratio in the range of 1.5 to 1.67.

EXAMPLE 3

Collagen Processing

Insoluble collagen granules (Sigma) were used as the starting material. Approximately 10 g of insoluble collagen granules were placed in 100 ml of solution of acetic acid (50 mM). This mixture was allowed to sit for approximately 16 hours. The mixture is then mechanically sheared in a Waring commercial blender for 5 minutes. The mixture is then rapidly frozen in liquid nitrogen. Freezing assists the separation of the collagen fibers. The mixture was then allowed to thaw and refrozen in liquid nitrogen a second time. This process may be repeated as many times as is desired, but in the detailed example (to be described) it was done twice. After the last freezing cycle, the frozen mass is freeze dried. Freeze drying removes both water and acetic acid such that, if the collagen is immersed in water at a liquid-to-solid weight ratio of 1 after drying is complete, the pH does not drop below 5.5. A microstructure typical of that developed is shown in FIG. 2.

EXAMPLE 4

Composite Formation

Collagen, treated as described above in Example 3 was mixed with the polymineralic hydroxyapatite precursor particles also as described above in Example 1. Three proportions, expressed in terms of the hydroxyaptite:collagen volume ratios, of 2:1, 5:1 and 10:1 were constituted. A typical mix weighs 50 grams. The proportions of $Ca(H_2PO_4)_2.H_2O$ and $Ca_4(PO_4)_2O$ used to produce the polymineralic particles are selected to produce calcium deficient hydroxyapatite, $Ca_9HPO_4(PO_4)_5OH$, at complete reaction, see EQ [1] and Example 1.

The rate of composite formation is illustrated in FIG. 4. The figure shows the manner in which heat is evolved during hydroxyapatite formation at physiological temperature by the reaction shown in EQ [1]. The presence of the collagen network can be seen to accelerate hydroxyapatite formation. The extent of acceleration increases with increasing proportion of collagen. Reaction is complete in 2.5 hours when the hydroxyapatite:collagen volume ratio is 2:1. The templating effect exerted by the collagen is shown in FIG. 3. The hydroxyapatite is formed in intimate association with the collagen network with the development of composite with substantial interconnected porosity. The rate of hydroxyapatite formation, as measured by the rate of heat evolution is accelerated in the presence of the collagen. This demonstrates that the collagen present is more than a filler. Companion X-ray diffraction analyses confirm the formation of hydroxyapatite. In contrast, if gelatin, which is denatured collagen, is used, no acceleration in the rate of hydroxyapatite formation is observed [TenHuisen and Brown, J. Biomed. Mater. Res. (1994)]. The rate of hydroxyapatite formation can be controlled by adding dilute concentrations of biocompatible organic acids to the reactant solution. This is illustrated in FIGS. 5A and 5B which shows the effects of acetic and citric acids on the rates of hydroxyapatite formation. However, neither of these were used in the composite formed in this example.

The composites were cast into bars approximately ¼×⅜×⅞ inch in dimension. These were tested in 3-point bend by supporting the bars at point approximately ¼ of the way from each end and applying a stress in the middle. The mechanical properties developed by the composite are in the range of those reported for bone. A very broad range of values have been reported for the mechanical properties of bone. The yield strength of wet bone under flexural loading ranges from about 10 to about 100 MPa. The yield strength of composites made by the methods described vary from about 7 to 12.5 MPa. However, these are the values attained in composites in which the fibrils are randomly oriented and better mechanical properties can be achieved by orienting the collagen fibrils. Young's Modulus of wet bone is reported to vary from about 283 MPa to 4 GPa. The modulus for the hydroxyapatite-collagen composite varies from 200 MPa to 1.7 GPa.

The mechanical failure characteristics exhibited by the composites indicate that toughness beyond that of hydroxyapatite is achieved are encouraging. While fracture of pure hydroxyapatite bars occurs elastically and catastrophically the composites demonstrate stable crack growth under tensile conditions. The stress-strain curves do not exhibit a discontinuity during yielding. The following values of work to fracture for hydroxyapatite, hydroxyapatite-collagen composites and natural bone may be compared: $0.07$ $KJ/m^2$ for hydroxyapatite, $0.51$ $KJ/m^2$ for hydroxyapatite-collagen composite produced by the method described (hydroxyapatite:collagen volume ratio 5:1), $0.2$ $KJ/m^2$ for tympanic bulla of whale, and $1.70$ $KJ/m^2$ for cow femur. A final point with respect to property development is that of the potential for clinical acceptance. Composites are prepared by reaction with water at 38° C. For property development studies the reactants were molded into bars and disks and allowed to react in a water vapor saturated atmosphere. A generally similar procedure could be used in an operating theater. Both the rate and extent of property development can be adjusted to meet specific needs.

EXAMPLE 5

Animal Studies

Animal studies involving rats have demonstrated that bone will intergrow into the phase pure hydroxyapatite composites formed by the methods described. In this study, 0.7 cm holes were excavated in the skulls of rats. These holes were then filled with the composite reactants. The reactants were hand mixed with distilled water in a liquid-to-total solids ratio of approximately 1. This mixture was then patted into the holes with light pressure and the wounds sutured. This is generically typical of the procedures for in vivo applications. After the animals were sacrificed at periods of time ranging to 12 weeks the bone-composite interfaces were examined. Depending on formulation, the implants retained their integrity and intergrowth was observed or the implant had resorbed.

EXAMPLE 6

Hydroxyapatite prepared by mixing the polymineralic particles of example 1 with water in the absence of collagen achieved a compressive strength of 175 MPa when measured at 24 hours after mixing.

EXAMPLE 7

HAp/Collagen Composition 100 gm polymineralic precursor particles of HAp prepared according to Example 1 are mixed with 4.7 gm of treated collagen prepared according to Example 3 (solid component.) 3 gm of the solid component are mixed with 1.2 gm of normal saline USP (a liquid-to-total solids weight ratio of 0.4) for two minutes at room temperature. The resultant composition is surgically implanted into a 15 mm cranial defect in a New Zealand white rabbit.

Visual examination of the implant after 4 months shows that the synthetic bone material was firmly attached to native bone and that it was invaded by blood vessels. There is no evidence indicating the formation of a fibrous tissue capsule isolating the implant from surrounding bone which would likely occur if the implant was regarded as foreign. Vascular invasion is indicative that the pore structure of the implant exhibited characteristics necessary to be partially or completely replaced, over time, by native bone tissue.

This study shows that HAp (with collagen) can be constituted so that it does not completely resorb in 4 and ½ months.

EXAMPLE 7A

HAp/Collagen Composition Containing Tobramycin Sulfate 100 gm polymineralic precursor particles of HAp prepared according to Example 1 are mixed with 4.7 gm of treated collagen prepared according to Example 3 (solid component). A stock saline solution of tobramycin sulfate is prepared by dissolving 40 mg tobramycin sulfate per ml of normal saline. 1.2 gm of the tobramycin sulfate-containing saline (liquid component) is added to 3.0 gm of the solid component to form a mixture (a liquid-to-total solids weight ratio of 0.4). The mixture is mixed for 2 minutes at room temperature and surgically implanted into a 15 mm cranial defect in a New Zealand white rabbit. The tobramycin sulfate-to HAp weight ratio is approximately 16 mg of tobramycin sulfate per gram of phase pure HAp.

EXAMPLE 8

HAp Containing Tobramycin Sulfate

Polymineralic precursor particles of HAp are prepared according to Example 1 to produce calcium deficient HAp (Ca/P=1.5) (solids component). No treated collagen was used in this example. 1.02 gm of the tobramycin sulfate stock saline solution prepared according to Example 7A is mixed with 3.0 gms of the solid component (a liquid-to-total solids weight ratio of 0.34) for two minutes at room temperature. The composition is surgically implanted in 15 mm cranial defects in a New Zealand white rabbit.

Thus, a wide range of rates of antibiotic release (designed to maintain a release rate in the therapeutic range of a selected period of time) can be achieved.

EXAMPLE 9

HAp/Collagen+HAp-Coated $CaHPO_4$ Filler to Control Porosity

Coating of $CaHPO_4$ filler particles with HAp is carried out as follows: 100 gm of $CaHPO_4$ particles having a particle size of 35 $\mu$m are placed in 400 ml of distilled water and stirred slowly. After about 16 hours, when the pH of the water reaches approximately 4.6, the produced HAp-coated $CaHPO_4$ filler particles are filtered from solution using filter paper and a Buchner funnel. These HAp-coated $CaHPO_4$ filler particles are then washed with approximately 100 ml of distilled water and dried in a desiccator over Drierite ($CaSO_4 \cdot \frac{1}{2}H_2O$). At the time of surgery, 0.9 gm of normal saline solution is mixed with 1.2 gm of HAp-coated $CaHPO_4$ filler particles and with 1.8 gm of a mixture of solid components containing polymineralic precursor particles of HAp prepared according to Example 1 and treated collagen prepared according to Example 3 wherein said mixture was obtained by mixing 100 gm of polymineralic particles of HAp of Example 1 and 4.7 gm of treated collagen of Example 3. The liquid-to-total solids (solids component+filler) weight ratio is 0.30. Mixing of the liquid and the total solids was carried out for 2 minutes at room temperature. The resultant composition is surgically implanted in 15 mm cranial defect in a New Zealand white rabbit.

EXAMPLE 10

HAp/Collagen+FAp-Coated $CaHPO_4$ Filler to Control Porosity and Delivery Fluoride Coating of $CaHPO_4$ filler particles with fluoroapatite (FAp) is carried out as follows: 200 gm of $CaHPO_4$ particles having a particle size of 35 $\mu$m are placed in 1000 ml of distilled water to which 0.44 gm of NAF has been added and stirred slowly for 16 hours at room temperature. The produced FAp-coated $CaHPO_4$ filler particles are filtered from solution using filter paper and a Buchner funnel. These FAp-coated $CaHPO_4$ filler particles are then washed with approximately 200 ml of distilled water and dried in a desiccator over Drierite ($CaSO_4 \cdot \frac{1}{2}H_2O$). At the time of surgery, 0.9 gm of normal saline solution is mixed with 1.2 gm of FAp-coated $CaHPO_4$ filler particles and with 1.8 gm of a mixture of solid components containing polymineralic precursor particles of HAp prepared according to Example 1 and treated collagen prepared according to Example 3 wherein said mixture was obtained by mixing 100 gm of polymineralic particles of HAp of Example 1 and 4.7 gm of treated collagen of Example 3. The liquid-to-total solids (solids component+filler) weight ratio is 0.30. Mixing of the liquid and the total solids is carried out for 2 minutes at room temperature. The resultant composition is surgically implanted in 15 mm cranial defect in 2 New Zealand white rabbits.

EXAMPLE 11

HAp/Collagen+HAp-Coated $Ca_4(PO_4)_2O$ Filler to Control Porosity

Coating of 57 $\mu$m $Ca_4(PO_4)_2O$ particles (TetCP) with $CaHPO_4$ is carried out as follows: 57.6 gm of 85% $H_3PO_4$ solution are mixed with approximately 400 ml of distilled water and heated to 80° C. 412 gm of 57 $\mu$m $Ca_4(PO_4)_2O$ particles are rapidly added to the $H_3PO_4$ solution while stirring. The solution is stirred for 4 hours at 80° C. after which the particles are filtered from this 80° C. solution using filter paper and a Buchner funnel. These $CaHPO_4$-coated $Ca_4(PO_4)_2O$ filler particles are then dried in a desiccator over Drierite ($CaSO_4 \cdot \frac{1}{2}H_2O$). At the time of surgery, 0.9 gm of normal saline solution is mixed with 1.2 gm of $CaHPO_4$-coated TetCP filler particles and with 1.8 gm of a mixture of solid components containing polymineralic precursor particles of HAp prepared according to Example 1 and treated collagen prepared according to Example 3 wherein said mixture was obtained by mixing 100 gm of polymineralic particles of HAp of Example 1 and 4.7 gm of treated collagen of Example 3. The liquid-to-total solids (solids component+filler) weight ratio is 0.30. The liquid used is normal saline. Mixing of the liquid and the total solids is carried out for 2 minutes at room temperature. The resultant composition is surgically implanted in 15 mm cranial defect in a New Zealand white rabbit.

In contrast to the $CaHPO_4$ filler (Ca/P=1) of Example 9 which is acidic, the composite TetCP/$CaHPO_4$ filler Ca/P=1.8) used in this experiment is basic. The Ca/P ratio of 1.8 was selected because this ratio approximates the ratio in bone. This ratio was also selected because HAp formation at this ratio will theoretically take up carbonate. This composite filler has the theoretical capacity to form HAp by reaction in physiological fluids without added water. As a consequence, the implant should contain a lower proportion of porosity when the filler present has reacted to form HAp.

EXAMPLE 12

HAp/Collagen+HAp-Coated $Ca_4(PO_4)_2O$ Filler to Control Porosity

The above experiment in Example 11 is repeated except the proportions of constituents are changed to: 0.9 gm of normal saline solution is mixed with 1.8 gm of $CaHPO_4$-coated TetCP filler particles and with 1.2 gm of a mixture of solid components containing polymineralic precursor particles of HAp prepared according to Example 1 and treated collagen prepared according to Example 3 wherein said mixture was obtained by mixing 100 gm of polymineralic particles of HAp of Example 1 and 4.7 gm of treated collagen of Example 3. The liquid-to-total solids (solids component+filler) weight ratio is 0.30. The liquid used is normal saline. Mixing of the liquid and the total solids was carried out for 2 minutes at room temperature. The resultant composition is surgically implanted in 15 mm cranial defect in 2 New Zealand white rabbits.

EXAMPLE 13

Preparation of Polymineralic Precursor Particles Capable of Forming HAp Having a Ca/P Ratio of 1.67 (Stoichiometric HAp)

In a typical run to prepare polymineralic particle precursors of hydroxyapatite which will be employed to form $Ca_{10}(PO_4)_6(OH)_2$ in vivo, 127 g of $Ca(H_2PO_4).H_2O$ are reacted with 640 g of $Ca_4(PO_4)_2O$. The $Ca_4(PO_4)_2O$ is prepared by firing an intimate mixture of equimolar amounts of $CaCO_3$ and $CaHPO_4$ powders to 1400° C. for 4 hours. After cooling the $Ca_4(PO_4)_2O$ is ground to an average particle size of 2–5 $\mu$m using standard powder preparation techniques. This material is then reacted with the acidic phosphate source $Ca(H_2PO_4).H_2O$, which is commercially available, by placing it and $Ca_4(PO_4)_2O$ in a 2-liter polyethylene bottle with approximately 600 ml of heptane.

Approximately 325 g of zirconia or alumina, or 130 g polycarbonate pellets are added and the bottle is sealed. The presence of the pellets limits agglomeration. This bottle is then placed in any shaking or rolling device. In the reaction, all of the $Ca(H_2PO_4).H_2O$ and some of the $Ca_4(PO_4)_2O$ are consumed in the formation of the polymineralic precursor particles comprising $Ca_4(PO_4)_2O$ and $Ca_x(PO_4)_y$. These produced polymineralic particles can then react rapidly in the presence of water to form hydroxyapatite in vivo.

After reaction, the slurry of polymineralic particles and the pellets is placed on a filter funnel and the bulk of the heptane is removed by vacuum suction and can be reused after distillation. The pellets are then removed by hand picking. Any material which adheres to pellets is removed by washing in heptane. Heptane not removed by vacuum suction is allowed to evaporate, either at room or slightly elevated temperature. Evaporation may also be carried out in vacuum.

3 grams of polymineralic particle precursors of stoichiometric HAp are mixed with 1.2 gm of normal saline solution for 2 minutes at room temperature. The liquid-to-total solids weight ratio is 0.4. The resultant composition is surgically implanted in 15 mm cranial defects in 2 New Zealand white rabbits.

EXAMPLE 13A

The above experiment in Example 13 is repeated except that the liquid-to-total solids weight ratio was reduced to 0.36. The mixture is implanted in 15 mm cranial defects in a New Zealand white rabbit.

EXAMPLE 14

In this experiment, a 1.8 gm of polymineralic precursor particles of stoichiometric HAp prepared according to Example 13 were mixed with 1.2 gm of FAp-coated $CaHPO_4$ filler prepared according to Example 10, and 0.75 gm normal saline (a liquid-to-total solids weight ratio of 0.25). The mixture is implanted in 15 mm cranial defects in 2 New Zealand white rabbits.

EXAMPLE 15

HAp–HEDP

Bisphosphonates are of interest as therapeutic agents to control the rate of bone resorption and the rate of tooth decay. A bisphosphonate, HEDP (1-hydroxyethylidene-1,1-diphosphonic acid) $C_2H_8P_2O_7$, saline stock solution was prepared by mixing 2.5 gm of HEDP with 1000 ml of normal saline solution. 1.2 gm of the HEDP-containing saline solution was mixed with 3 grams of a mixture of solid components containing polymineralic precursor particles of HAp prepared according to Example 1. The liquid-to-total solids weight ratio is 0.4. The resultant composition is surgically implanted in 15 mm cranial defects in 2 New Zealand white rabbits.

The HEDP-to-HAp weight ratio can be adjusted in three ways: (1) a larger amount of HEDP can be added to the saline solution, (2) the liquid-to-solids ratio can be increased, (3) the HEDP powder can be intermixed with the polymineralic particles prior to the addition of the liquid.

What is claimed is:

1. A synthetic bone-like substitute kit comprising:
   (a) a container of polymineralic precursor particles produced by reacting a calcium source, with an acidic phosphate source having at least two protons attached to one phosphate, in a non-aqueous liquid for a time sufficient to produce polymineralic precursor particles capable of forming hydroxyapatite without additional sources of calcium or phosphate said polymineralic precursor particles having a Ca/P ratio of 1.5 to 1.67, capable of forming hydroxyapatite in the absence of additional sources of calcium and phosphate.

2. The kit according to claim 1 further comprising a container of a polymeric material capable of promoting mineralization of hydroxyapatite.

3. The kit according to claim 1 wherein said polymineralic material is treated insoluble collagen having a pore size of from 2 to 100 $\mu$m.

4. The invention according to claim 1 wherein said calcium source is calcium oxide, calcium carbonate, calcium hydroxide, calcium hydroxide-calcium carbonate double salts, or a basic calcium phosphate having a Ca/P ratio greater than 1.67 or mixtures thereof.

5. A method of treating insoluble collagen for use in a synthetic bone-like composition which comprises the steps of:
   (a) suspending insoluble collagen in an acidic solution to form a suspension;
   (b) subjecting said suspension to a mechanical action;
   (c) freezing said suspension;
   (d) thawing said frozen suspension; and
   (e) collecting said treated collagen.

6. The method according to claim 5 wherein said treated collagen has a pore size from 2 $\mu$m to 100 $\mu$m.

7. The method according to claim 5 further comprising repeating steps (c) and (d), prior to step (e).

8. The method according to claim 5, wherein said collecting step (e) is freeze-drying.

9. Insoluble collagen produced by the process according to claims 5 or 6.

10. A method of producing polymineralic precursor particles capable of forming hydroxyapatite in the absence of additional sources of calcium and phosphate, which comprises the steps of:

(a) reacting at least one calcium source, with at least one acid phosphate source having at least 2 protons attached to one phosphate, in a non-aqueous liquid for a time sufficient to form said polymineralic precursors particles and having a Ca/P ratio of 1.5 to 1.67; and (b) collecting said polymineralic precursor particles.

11. The method according to claim 10 wherein said calcium source has an average particle size of from 1 μm to 5 μm.

12. The method according to claim 10 wherein said non-aqueous liquid is selected from the group consisting of substituted or unsubstituted liquid aliphatic hydrocarbons and liquid aromatic hydrocarbons.

13. The method according to claim 10 wherein said calcium source is selected from the group consisting of calcium oxide, calcium carbonate, calcium hydroxide, calcium hydroxide-calcium carbonate double salts, or a basic calcium phosphate having a Ca/P ratio of greater than 1.67 or mixtures thereof.

14. The method according to claim 10 wherein said acidic phosphate source having at least two protons attached to one phosphate is selected form the group consisting of phosphoric acid, $H_3PO_4$, $H_3PO_4 \cdot \frac{1}{2}H_2O$, $Ca(H_2PO_4)_2$, $Ca(H_2PO_4)_2 \cdot H_2O$ and $NH_4H_2(PO_4)_2 \cdot nH_2O$, or mixtures thereof.

15. The method according to claim 10 wherein said collecting step (b) comprises evaporating off said non-aqueous liquid.

16. Polymineralic precursor particles produced by the process according to claim 10.

17. A hydroxyapatite composition comprising the polymineralic precursor particles according to claim 16.

18. The composition according to claim 17, which completely reacts to form phase pure hydroxyapatite within 2 hours.

19. The method according to claim 8 wherein said calcium source is calcium oxide, calcium carbonate, calcium hydroxide, calcium hydroxide-calcium carbonate double salts, or a basic calcium phosphate having a Ca/P ratio greater than 1.67 or mixtures thereof.

20. The method according to claim 19 wherein said basic calcium phosphate is $Ca_4(PO_4)_2O$.

21. The method according to claim 8 wherein said basic calcium phosphate is $Ca_4(PO_4)_2O$ and the non aqueous liquid is an aliphatic hydrocarbon.

22. The method according to claim 10, wherein said non-aqueous liquid is heptane.

* * * * *